United States Patent
Takagaki et al.

(10) Patent No.: US 9,312,038 B2
(45) Date of Patent: Apr. 12, 2016

(54) X-RAY DIAPHRAGM MECHANISM AND X-RAY CT APPARATUS

(75) Inventors: Norifumi Takagaki, Tokyo (JP); Tsutomu Suzuki, Tokyo (JP); Mikio Mochitate, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 182 days.

(21) Appl. No.: 14/115,491

(22) PCT Filed: May 30, 2012

(86) PCT No.: PCT/JP2012/063845
§ 371 (c)(1),
(2), (4) Date: Nov. 4, 2013

(87) PCT Pub. No.: WO2012/165450
PCT Pub. Date: Dec. 6, 2012

(65) Prior Publication Data
US 2014/0079179 A1    Mar. 20, 2014

(30) Foreign Application Priority Data

May 31, 2011  (JP) ................. 2011-121682

(51) Int. Cl.
*G21K 1/04* (2006.01)
*A61B 6/06* (2006.01)
(Continued)

(52) U.S. Cl.
CPC . *G21K 1/046* (2013.01); *A61B 6/06* (2013.01); *G01N 23/046* (2013.01); *G21K 1/04* (2013.01); *A61B 6/035* (2013.01)

(58) Field of Classification Search
CPC ........ A61B 6/035; A61B 6/06; G01N 23/046; G21K 1/04; G21K 1/046
See application file for complete search history.

(56) References Cited

U.S. PATENT DOCUMENTS

| | | | | |
|---|---|---|---|---|
| 4,361,902 A * | 11/1982 | Brandt | ............... | G21K 1/04 378/150 |
| 6,445,764 B2 * | 9/2002 | Gohno | ............... | G21K 1/04 378/150 |

(Continued)

FOREIGN PATENT DOCUMENTS

| JP | 6-64613 | 9/1994 |
|---|---|---|
| JP | 2011-36641 | 2/2011 |

OTHER PUBLICATIONS

International Search Report in PCT/JP2012/063845.

*Primary Examiner* — Wyatt Stoffa
(74) *Attorney, Agent, or Firm* — Cooper & Dunham LLP

(57) ABSTRACT

The present invention includes: X-ray shielding materials; X-ray shielding material mounting plates to which the X-ray shielding portions are fixed; a driven side link and a driving side link that connect the two X-ray shielding material mounting plates to each other so that the X-ray shielding portions face each other and cross each other; connecting portions that connect each of the X-ray shielding material mounting plates to the driven side link and the driving side link; and a driving device that drives the driving side link so as to rotate. Connecting portions and are provided at positions not interfering with a movable region of the X-ray shielding material mounting plates formed in conjunction with the rotational driving of the driven side link and the driving side link. The X-ray shielding material mounting plates are moved by the rotational driving of the driving side link and accordingly, the slit width between the X-ray shielding materials is changed.

10 Claims, 11 Drawing Sheets

(51) Int. Cl.
*G01N 23/04* (2006.01)
*A61B 6/03* (2006.01)

(56) References Cited

U.S. PATENT DOCUMENTS

| | | | |
|---|---|---|---|
| 6,707,876 B2* | 3/2004 | Tanigawa | A61B 6/032 378/19 |
| 7,023,962 B2* | 4/2006 | Xu | G21K 1/04 378/147 |
| 2005/0025278 A1* | 2/2005 | Hagiwara | A61B 6/032 378/7 |
| 2007/0086576 A1* | 4/2007 | Yang | A61B 6/06 378/152 |
| 2011/0038466 A1* | 2/2011 | Junjie | G21K 1/04 378/153 |
| 2014/0146949 A1* | 5/2014 | Pan | A61B 6/06 378/152 |

* cited by examiner

Prior Art

X-RAY DIAPHRAGM MECHANISM AND X-RAY CT APPARATUS

TECHNICAL FIELD

The present invention relates to an X-ray diaphragm mechanism and an X-ray CT apparatus and in particular, to an X-ray diaphragm mechanism when two X-ray shielding plates are used.

BACKGROUND ART

PTL 1 discloses two X-ray shielding plates which are formed in concave shapes and in which recessed sides of the concave shapes are disposed so as to face each other, a link that connects protruding portions at both ends, and an X-ray diaphragm mechanism capable of adjusting a slit width by rotating the central portion of the link.

CITATION LIST

Patent Literature

[PTL 1] JP-A-5-76523

SUMMARY OF INVENTION

Technical Problem

In the X-ray diaphragm mechanism described above, however, when the two X-ray shielding plates are mounted so as to cross each other with a difference in level therebetween, the X-ray shielding plates interfere with each other in a movable region. Accordingly, there has been a problem in that an arbitrary slit width cannot be realized.

This problem will be described with reference to FIG. 11. FIG. 11 is a state transition diagram of an X-ray diaphragm for explaining the background art. (a) shows an X-ray diaphragm mechanism 20 when the slit width is a maximum width, (b) shows the X-ray diaphragm mechanism 20 when the slit width is narrower than (a), (c) shows the X-ray diaphragm mechanism 20 when the slit width is narrower than (b), and (d) shows the X-ray diaphragm mechanism 20 when the slit width is a minimum width (at the time of closing). The X-ray diaphragm mechanism 20 includes X-ray shielding materials 21a and 21b, a driving side link 25b that is fixed to a rotary shaft 23 of a motor 24 and is driven to rotate by the motor 24, and a driven side link portion 25a that follows the driving side link 25b. One-side ends (in FIG. 11, left sides) of the X-ray shielding materials 21a and 21b are connected to the driving side link portion 25b through connecting portions 22a and 22b, respectively. The other ends (in FIG. 11, right sides) of the X-ray shielding materials 21a and 21b are connected to the driven side link portion 25a through connecting portions 26a and 26b, respectively. When the driving side link 25b starts to be rotated from the state of (a) by the motor 24, the driving side link 25b starts counterclockwise rotation (left rotation) in FIG. 11, and the X-ray shielding materials 21a and 21b are brought close to each other. Accordingly, the slit width becomes narrow. When the driving side link 25b is further rotated for state transition to (b), (c), and (d), the connecting portion 22b and the X-ray shielding material 21a or the connecting portion 26b and the X-ray shielding material 21b interfere with each other in a movable region.

Therefore, although the states (c) and (d) are shown in FIG. 11 for the purpose of explanation, the rotation of the driving side link 25b is actually stopped when the connecting portion 22b and the X-ray shielding material 21a or the connecting portion 26b and the X-ray shielding material 21b interfere with each other, that is, in the middle of the transition from (b) to (c). For this reason, there has been a problem in that the slit width cannot be narrowed past this point.

In view of the above-described problem, it is an object of the present invention to provide an X-ray diaphragm mechanism capable of realizing an arbitrary slit width without interference between X-ray shielding plates and links for connecting the X-ray shielding plates in each movable region and an X-ray CT apparatus in which the X-ray diaphragm mechanism is mounted.

Solution to Problem

In order to achieve the above-described object, an X-ray diaphragm mechanism according to the present invention is characterized in that two X-ray shielding materials crossing the driving region of a link, which is driven to rotate by a motor, are assembled to the link by providing a sufficient distance between each X-ray shielding plate and a link so that the two X-ray shielding materials do not interfere with each other at any slit width.

More specifically, an X-ray diaphragm mechanism according to the present invention includes: two X-ray shielding members each including an X-ray shielding portion for shielding from X-rays, a first peripheral portion located on one end side of the X-ray shielding portion in a longitudinal direction, and a second peripheral portion located on the other end side of the X-ray shielding portion in the longitudinal direction; a first link for connecting the first peripheral portions of the X-ray shielding members so as to cross each other in a state where the X-ray shielding portions of the X-ray shielding members face each other and a second link for connecting the second peripheral portions of the X-ray shielding members so as to cross each other in a state where the X-ray shielding portions of the X-ray shielding members face each other; a first connecting portion that connects the first peripheral portion of each X-ray shielding member and the first link to each other and a second connecting portion that connects the second peripheral portion of each X-ray shielding member and the second link to each other; and a driving device that drives the first link or the second link so as to rotate. A slit width between the X-ray shielding portions of the two X-ray shielding members is changed by moving the two X-ray shielding members in conjunction with rotational driving of the first and second links, and the first and second connecting portions are provided at positions not interfering with a movable region of the X-ray shielding member.

In addition, an X-ray CT apparatus according to the present invention includes: the X-ray diaphragm mechanism described above; an X-ray generation unit that generates X-rays; an X-ray detector that detects the X-rays and outputs an image signal; a rotation unit that rotates in a state where the X-ray generation unit, the X-ray diaphragm mechanism, and the X-ray detector are mounted; and an image reconstruction unit that generates a reconstructed image by performing image reconstruction processing on the basis of the image signal. The X-ray diaphragm mechanism limits an irradiation range of X-rays generated from the X-ray generation unit.

Advantageous Effects of Invention

As described above, by providing a sufficient distance between the X-ray shielding plate and the link so that the rotational driving region of the link, which is driven to rotate by the motor, and the movable region of the X-ray shielding plate do not interfere with each other in any slit width when two X-ray shielding plates are mounted so as to cross each other with a difference in level therebetween, it is possible to realize an arbitrary slit width without interference of the X-ray shielding plates in the movable region.

BRIEF DESCRIPTION OF DRAWINGS

FIG. 10 is a state transition diagram using a partially enlarged perspective view of the X-ray diaphragm mechanism 103 according to a fourth embodiment, where (a) shows a state when the slit width is a minimum (complete shielding state) and (b) shows a state where a stud 8s has moved into a clearance groove 7a.

DESCRIPTION OF EMBODIMENTS

Figure 1:
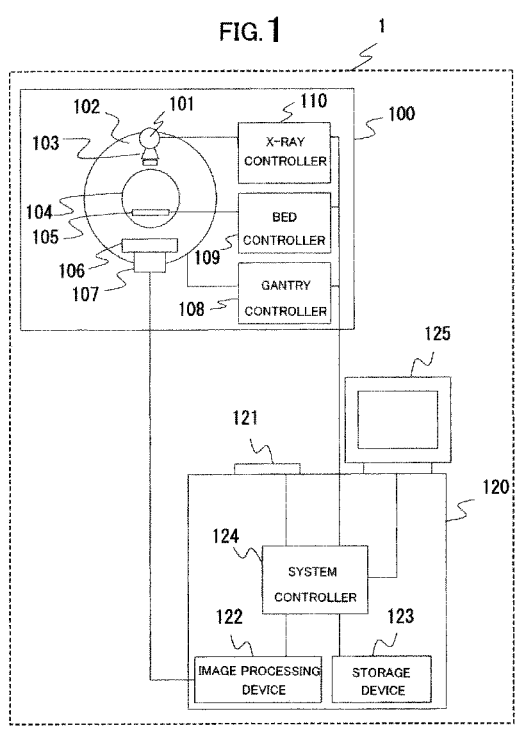
FIG. 1 is a diagram showing the overall configuration of an X-ray CT apparatus 1 according to the present embodiment.

Hereinafter, embodiments of the present invention will be described with reference to the accompanying drawings. Configurations having the same functions and procedures of the same processing content are denoted by the same reference numerals, and explanation thereof will not be repeated.

First, based on FIG. 1, the schematic configuration in an example of an X-ray CT apparatus according to the present embodiment will be described. FIG. 1 is a diagram showing the overall configuration of an X-ray CT apparatus 1 according to the present embodiment. The X-ray CT apparatus 1 includes a scan gantry unit 100 and a console 120. The scan gantry unit 100 includes an X-ray tube 101, a rotary disk 102, a collimator (also referred to as an X-ray diaphragm mechanism) 103, an X-ray detector 106, a data acquisition system 107, a bed 105, a gantry controller 108, a bed controller 109, and an X-ray controller 110. The X-ray tube 101 is a device that emits X-rays to an object placed on the bed 105. The collimator 103 is a device for limiting the emission range of X-rays emitted from the X-ray tube 101. The rotary disk 102 includes an opening 104 through which the object placed on the bed 105 is inserted and also includes the X-ray tube 101 and the X-ray detector 106 mounted therein and rotates around the object. The X-ray detector 106 is a device that is disposed opposite the X-ray tube 101 and measures the spatial distribution of transmitted X-rays by detecting X-rays transmitted through the object, and is formed by arraying a number of X-ray detection elements in the rotation direction of the rotary disk 102 or in a two-dimensional manner of the rotation direction of the rotary disk 102 and the rotation axis direction. The data acquisition system 107 is a device that collects the amount of X-rays detected by the X-ray detector 106 as digital data. The gantry controller 108 is a device that controls the rotation of the rotary disk 102. The bed controller 109 is a device that controls the bed 105 to move up and down and back and forth. The X-ray controller 110 is a device that controls electric power input to the X-ray tube 101.

The console 120 includes an input device 121, an image processing device 122, a display device 125, a storage device 123, and a system controller 124. The input device 121 is a device for inputting the name of the object, examination date and time, imaging conditions, and the like. Specifically, the input device 121 is a keyboard or a pointing device. The image processing device 122 is a device that reconstructs a CT image by performing arithmetic processing on the measurement data transmitted from the data acquisition system 107. The display device 125 is a device that displays the CT image created by the image processing device 122. Specifically, the display device 125 is a CRT (Cathode-Ray Tube), a liquid crystal display, or the like. The storage device 123 is a device that stores the data collected by the data acquisition system 107 and the image data of the CT image created by the image processing device 122. Specifically, the storage device 123 is a HDD (Hard Disk Drive) or the like. The system controller 124 is a device that controls these devices, the gantry controller 108, the bed controller 109, and the X-ray controller 110.

The X-ray controller 110 controls electric power input to the X-ray tube 101 on the basis of the imaging conditions input through the input device 121, in particular, an X-ray tube voltage, an X-ray tube current, and the like, so that the X-ray tube 101 emits X-rays to the object according to the imaging conditions. The X-ray detector 106 detects X-rays, which are emitted from the X-ray tube 101 and transmitted through the object, using a number of X-ray detection elements and measures the distribution of transmitted X-rays. The rotary disk 102 is controlled by the gantry controller 108, and rotates on the basis of the imaging conditions input through the input device 121, in particular, rotation speed and the like. The bed 105 is controlled by the bed controller 109, and operates on the basis of the imaging conditions input through the input device 121, in particular, the helical pitch and the like.

X-ray emission from the X-ray tube 101 and measurement of the distribution of transmitted X-rays by the X-ray detector 106 are repeated with the rotation of the rotary disk 102. As a result, projection data from various angles is acquired. The acquired projection data from various angles is transmitted to the image processing device 122. The image processing device 122 reconstructs a CT image by performing back projection processing on the transmitted projection data from various angles. The CT image obtained by reconstruction is displayed on the display device 125.

First Embodiment

Figure 2:
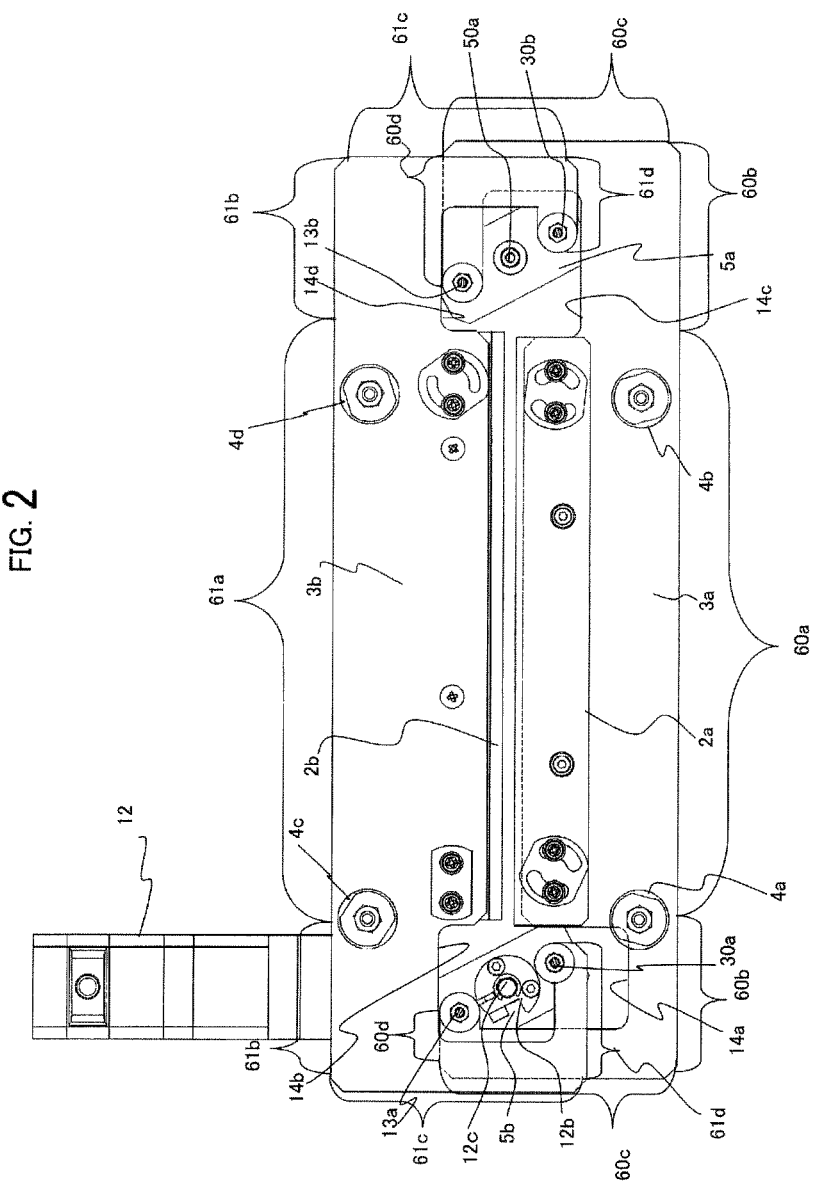
FIG. 2 is an enlarged plan view of an X-ray diaphragm mechanism 103 according to a first embodiment.
Figure 3:
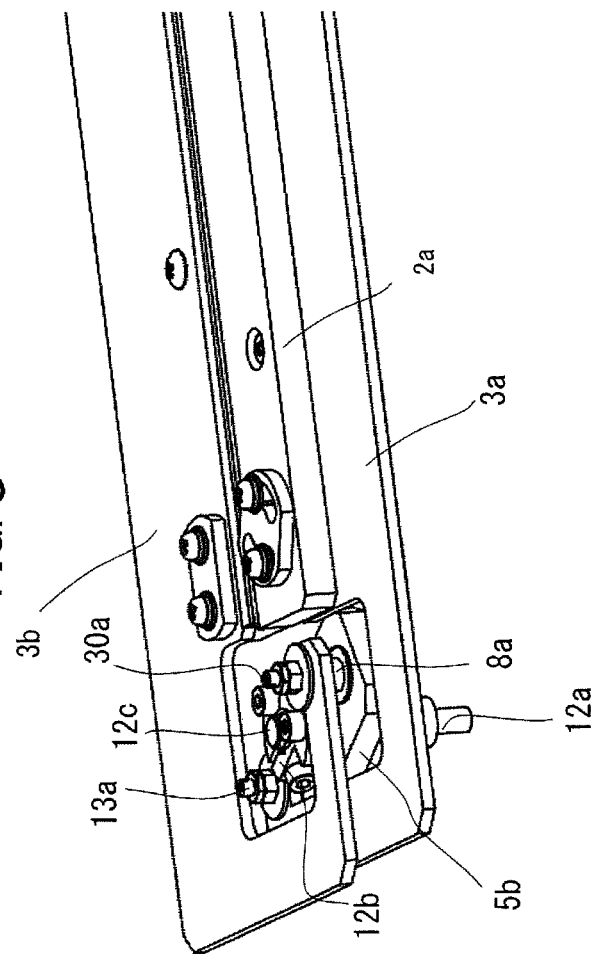
FIG. 3 is a partial perspective view of the X-ray diaphragm mechanism 103 according to the first embodiment.
Figure 4:
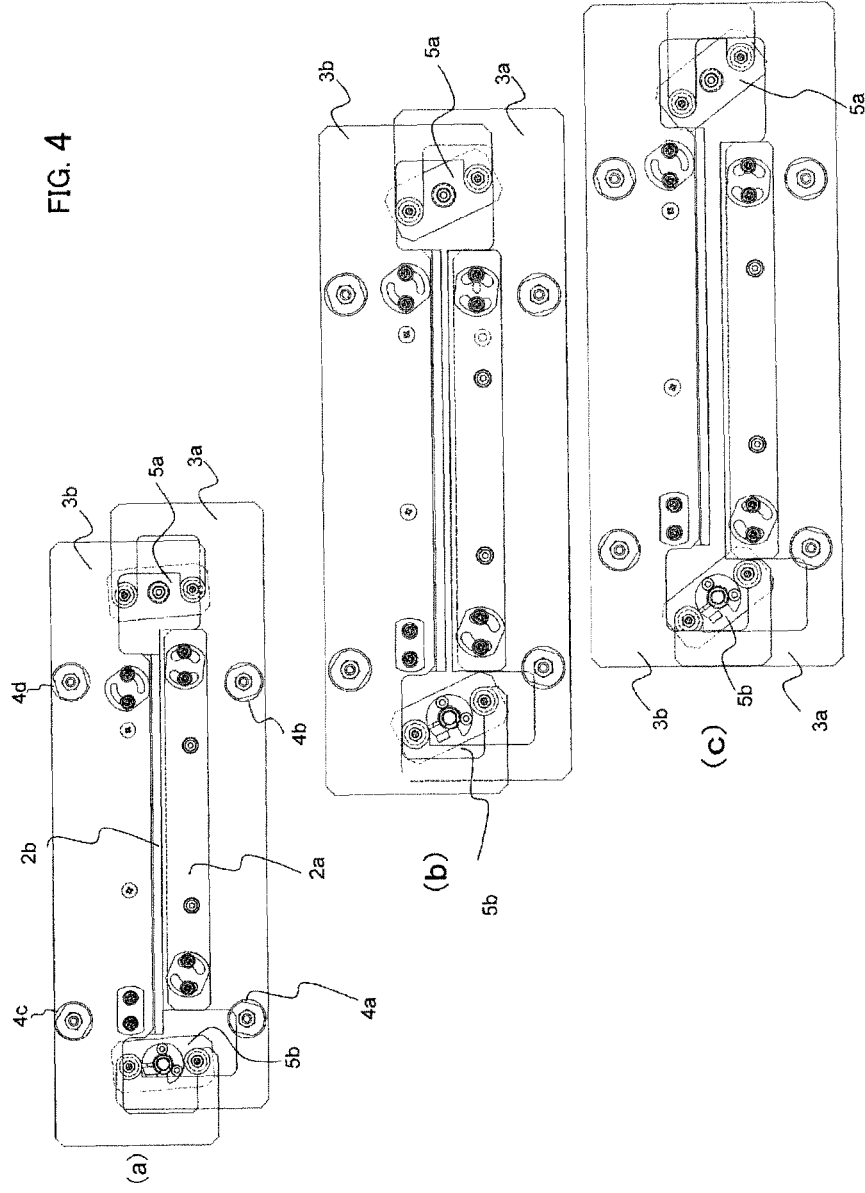
FIG. 4 is a state transition diagram showing, as a plan view, a state when the slit width of the X-ray diaphragm mechanism 103 according to the first embodiment changes, where (a) shows a state when the slit width is a minimum (complete shielding state), (b) shows a state between the maximum slit width and the minimum slit width, and (c) shows a state when the slit width is a maximum.
Figure 5:
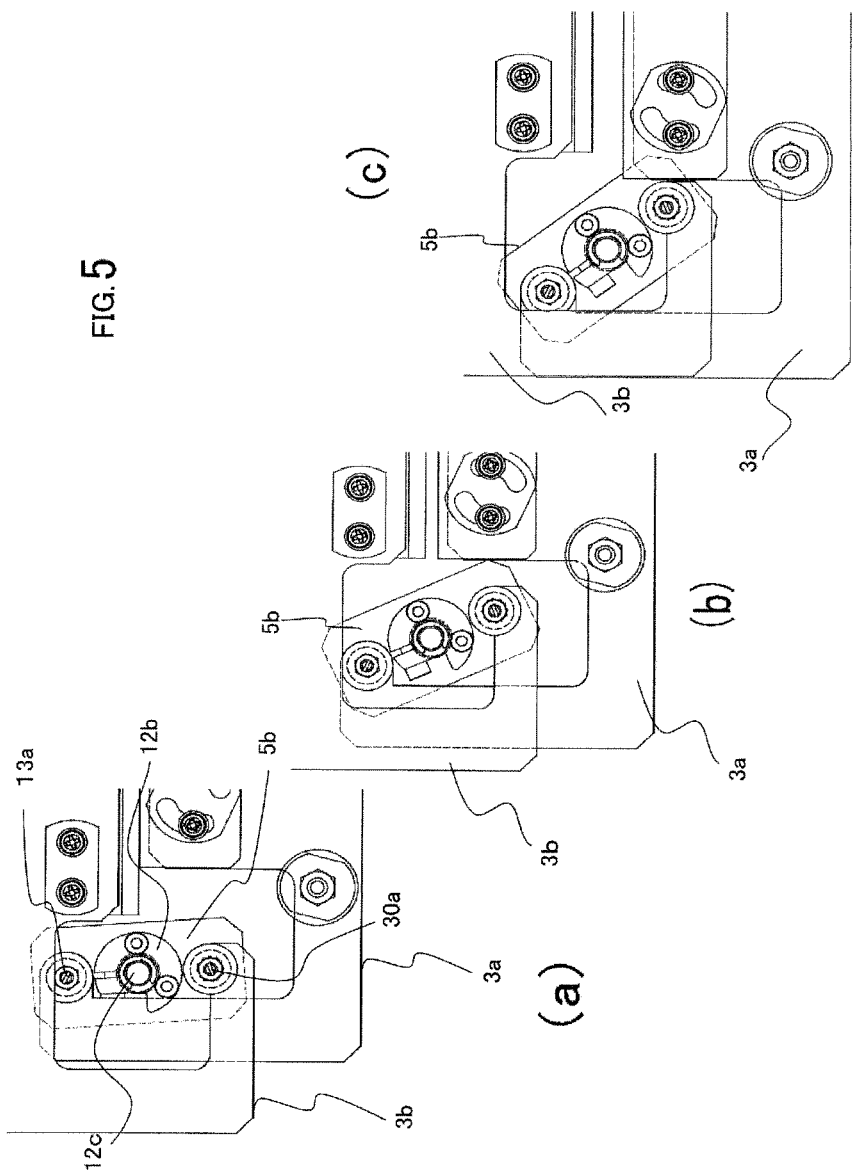
FIG. 5 is an enlarged state transition diagram near the end corresponding to the state transition diagram of FIG. 4, where (a) shows a state when the slit width is a minimum (complete shielding state), (b) shows a state between the maximum slit width and the minimum slit width, and (c) shows a state when the slit width is a maximum.

A first embodiment of the present invention will be described with reference to FIGS. 2 to 5. FIG. 2 is an enlarged plan view of the X-ray diaphragm mechanism 103 according to the first embodiment. FIG. 3 is a partial perspective view of the X-ray diaphragm mechanism 103 according to the first embodiment. FIG. 4 is a state transition diagram showing, as a plan view, a state when the slit width of the X-ray diaphragm mechanism 103 according to the first embodiment changes, where (a) shows a state when the slit width is a minimum (complete shielding state), (b) shows a state between the maximum slit width and the minimum slit width, and (c) shows a state when the slit width is a maximum. FIG. 5 is an enlarged state transition diagram near the end corresponding to the state transition diagram of FIG. 4, where (a) shows a state when the slit width is a minimum (complete shielding state), (b) shows a state between the maximum slit width and the minimum slit width, and (c) shows a state when the slit width is a maximum.

FIGS. 2, 4, and 5 are plan views of the X-ray diaphragm mechanism 103 when viewed toward the X-ray tube 101 from the bed 105, and FIG. 3 shows a partial perspective view of FIG. 2. End surfaces of X-ray shielding material mounting plates 3a and 3b facing the bed 105 are mainly drawn. The X-ray diaphragm mechanism 103 limits the X-ray emission range by adjusting the width of a slit, through which X-rays emitted from the X-ray tube 101 pass, by making X-ray shielding materials 2a and 2b for shielding from X-rays face the two X-ray shielding material mounting plates 3a and 3b for mounting the X-ray shielding materials 2a and 2b and increasing or decreasing a gap (hereinafter, referred to as a "slit") between the X-ray shielding material mounting plates 3a and 3b.

The X-ray diaphragm mechanism 103 includes the two X-ray shielding material mounting plates 3a and 3b each having an approximately concave shape. The X-ray shielding material mounting plate 3a includes a main body portion 60a extending in a longitudinal direction, which includes a region for mounting the X-ray shielding material 2a and two first arm portions 60b protruding, from both ends of the main body portion 60a along the longitudinal direction, in an opposite direction to a side where the main body portion 60a is located along the longitudinal direction. A second arm portion 60c protruding in a direction perpendicular to the longitudinal direction and toward a side where the facing X-ray shielding material mounting plate 3b is located is provided at the end of each first arm portion 60b not facing the main body portion 60a. A third arm portion 60d protruding toward a side where the main body portion 60a is located along the longitudinal direction is provided at the end of each second arm portion 60c not facing the first arm portion 60b. That is, cutout portions 14a and 14c formed of an opening surrounded by the first arm portion 60b provided at each end, the second arm portion 60c protruding from the first arm portion 60b, and the third arm portion 60d protruding from the second arm portion 60c are provided at both ends of the X-ray shielding material mounting plate 3a along the longitudinal direction.

The X-ray shielding material mounting plate 3b includes a main body portion 61a extending in a longitudinal direction including a region for mounting the X-ray shielding material 2b and two first arm portions 61b protruding, from both ends of the main body portion 61a along the longitudinal direction, in an opposite direction to a side where the main body portion 61a is located along the longitudinal direction. A second arm portion 61c protruding in a direction perpendicular to the longitudinal direction and toward a side where the facing X-ray shielding material mounting plate 3a is located is provided at the end of each first arm portion 61b not facing the main body portion 61a. A third arm portion 61d protruding in a direction in which the main body portion 61a is located along the longitudinal direction is provided at the end of each second arm portion 61c not facing the first arm portion 61b. That is, cutout portions 14b and 14d formed of an opening surrounded by the first arm portion 61b provided at each end, the second arm portion 61c protruding from the first arm portion 61b, and the third arm portion 61d protruding from the second arm portion 61c are provided at both ends of the X-ray shielding material mounting plate 3b along the longitudinal direction.

The X-ray shielding material mounting plates 3a and 3b are connected to each other through approximately plate-shaped links 5a and 5b. A motor 12 as a rotational driving device is provided near the link 5b. A shaft 12a rotated by the motor 12 is connected to a link rotation center 12c of the link 5b. A partially cut ring-shaped boss 12b is disposed around the link rotation center 12c, and is fixed to the link 5b. The link rotation center 12c is disposed in a hollow region of the boss 12b. In addition, the rotational driving force of the motor 12 is transmitted from the shaft 12a to the link rotation center 12c, and the link 5b is driven to rotate through the boss 12b. According to the rotational driving of the link 5b, the link 5a rotates around a link rotation center 50a. In the following explanation, the link 5b is referred to as the driving side link 5b, and the link 5a that is driven in conjunction with the rotational driving of the driving side link 5b is referred to as the driven side link 5a.

The open end of the third arm portion 60d located on the one end side of the X-ray shielding material mounting plate 3a (in FIG. 2, on a side close to the motor 12) is connected to the driving side link 5b through a connecting portion 13a, such as a screw. At the open end of the third arm portion 61d located on the one end side of the X-ray shielding material mounting plate 3b, there is a protruding portion that protrudes toward the second arm portion 61b. The protruding portion and the driving side link 5b are connected to each other through a collar 8a (refer to FIG. 3), which is a cylindrical member, and a connecting portion 30a, such as a screw. The connecting portion 30a passes through the cylindrical inside of the collar 8a, and connects the X-ray shielding material mounting plate 3b and the driving side link 5b to each other. That is, the X-ray shielding material mounting plates 3a and 3b are connected to each other through the driving side link 5b by providing a step equivalent to the height of the collar 8a for the driving side link 5b. In addition, a part of the second arm portion 60c located on the one end side of the X-ray shielding material mounting plate 3a and a part of the second arm portion 61c located on the one end side of the X-ray shielding material mounting plate 3b cross each other alternately (at different heights) since the second arm portion 61c is located on the side of the second arm portion 60c opposite the driving side link 5b.

The link rotation center 12c of the driving side link 5b is located in an opening (overlapping region of an opening formed by the cutout portions 14a and 14b) surrounded by the first arm portion 61b, the second arm portion 61c, and the third arm 61d of the X-ray shielding material mounting plate 3b and the second arm portion 60c and the third arm portion 60d of the X-ray shielding material mounting plate 3a. Accordingly, the link rotation center 12c of the driving side link 5b is located closer to the main body portions 60a and 61*a* than to a portion where the X-ray shielding material mounting plates 3*a* and 3*b* cross each other.

The open end of the third arm portion 60*d* located on the other end side of the X-ray shielding material mounting plate 3*a* is connected to the driven side link 5*a* through a connecting portion 13*b*, such as a screw. The driven side link 5*a* and the open end of the third arm portion 61*d* located on the other end side of the X-ray shielding material mounting plate 3*b* are connected to each other through a collar (not shown), which is a cylindrical member, and a connecting portion 30*b*, such as a screw. The collar (not shown) has the same height as the collar 8*a* described above. The connecting portion 30*b* passes through the cylindrical inside of the collar (not shown), and connects the X-ray shielding material mounting plate 3*b* and the driven side link 5*a* to each other. That is, the X-ray shielding material mounting plates 3*a* and 3*b* are connected to each other through the driven side link 5*a* by providing a step equivalent to the height of the collar (not shown), which is disposed between the driven side link 5*a* and the X-ray shielding material mounting plate 3*b*, for the driven side link 5*a*. In addition, a part of the second arm portion 60*c* located on the other end side of the X-ray shielding material mounting plate 3*a* and a part of the second arm portion 61*c* located on the other end side of the X-ray shielding material mounting plate 3*b* cross each other alternately (at different heights) since the second arm portion 61*c* is located on a side of the second arm portion 60*c* opposite the driven side link 5*a*.

The link rotation center 50*a* of the driven side link 5*a* is located in an opening (overlapping region of an opening formed by the cutout portions 14*c* and 14*d*) surrounded by the first arm portion 61*b*, the second arm portion 61*c*, and the third arm portion 61*d* of the X-ray shielding material mounting plate 3*b* and the first arm portion 60*b*, the second arm portion 60*c*, and the third arm portion 60*d* of the X-ray shielding material mounting plate 3*a*. Accordingly, the link rotation center 50*a* of the driven side link 5*a* is located closer to the main body portions 60*a* and 61*a* than to a portion where the X-ray shielding material mounting plates 3*a* and 3*b* cross each other.

The approximately plate-shaped X-ray shielding materials 2*a* and 2*b*, which are formed by using a member that can shield from X-rays, are fixed to the two X-ray shielding material mounting plates 3*a* and 3*b*, respectively. The X-ray shielding material 2*a* is fixed to a surface of the X-ray shielding material mounting plate 3*a* facing the X-ray shielding material mounting plate 3*b* (surface facing the bed 105) in a state where the two X-ray shielding material mounting plates 3*a* and 3*b* face each other. More specifically, the X-ray shielding material 2*a* is fixed to the side end of the X-ray shielding material mounting plate 3*b* in the main body portion 60*a* of the X-ray shielding material mounting plate 3*a* along the longitudinal direction of the main body portion 60*a* and in a state protruding toward the X-ray shielding material mounting plate 3*b* from the main body portion 60*a*.

The X-ray shielding material 2*b* is fixed to a surface of the X-ray shielding material mounting plate 3*b* facing the X-ray shielding material mounting plate 3*a* (surface facing the X-ray tube 101). In addition, the facing surfaces of the X-ray shielding materials 2*a* and 2*b* are mounted so as to form the same plane. More specifically, the approximately plate-shaped X-ray shielding material 2*b* that is formed by using a member that can shield from X-rays is fixed to the side end of the X-ray shielding material mounting plate 3*a* in the main body portion 61*a* of the X-ray shielding material mounting plate 3*b* along the longitudinal direction of the main body portion 61*a* and in a state protruding toward the X-ray shielding material mounting plate 3*a* from the main body portion 61*a*.

The cutout portion 14*a* of the X-ray shielding material mounting plate 3*a* described above is provided such that the rotational driving region of the connecting portion 13*a*, the connecting portion 30*a*, and the driving side link 5*b* at the time of rotational driving of the driving side link 5*b* does not interfere with the movable region of the X-ray shielding material mounting plate 3*a* according to the rotational driving of the driving side link 5*b*. In addition, the cutout portion 14*c* of the X-ray shielding material mounting plate 3*a* is provided such that the rotational driving region of the connecting portion 13*b*, the connecting portion 30*b*, and the driven side link 5*a* at the time of rotation of the driven side link 5*a* according to the rotational driving of the driving side link 5*b* does not interfere with the movable region of the X-ray shielding material mounting plate 3*a*.

The cutout portion 14*b* of the X-ray shielding material mounting plate 3*b* described above is provided such that the rotational driving region of the connecting portion 13*a*, the connecting portion 30*a*, and the driving side link 5*b* at the time of rotational driving of the driving side link 5*b* does not interfere with the movable region of the X-ray shielding material mounting plate 3*b* according to the rotational driving of the driving side link 5*b*. In addition, the cutout portion 14*d* of the X-ray shielding material mounting plate 3*b* is provided such that the rotational driving region of the connecting portion 13*b*, the connecting portion 30*b*, and the driven side link 5*a* at the time of rotation of the driven side link 5*a* according to the rotational driving of the driving side link 5*b* does not interfere with the movable region of the X-ray shielding material mounting plate 3*b*.

As described above, the X-ray shielding material mounting plates 3*a* and 3*b* can be connected to the driving side link 5*b* by bypassing the link rotation center 12*c* of the driving side link 5*b*, the connecting portion 13*a*, the collar 8*a*, and the connecting portion 30*a* so that the X-ray shielding material mounting plates 3*a* and 3*b* do not interfere with them. In addition, the X-ray shielding material mounting plates 3*a* and 3*b* can be connected to the driven side link 5*a* by bypassing the link rotation center 50*a* of the driven side link 5*a*, the connecting portion 13*b*, a collar (not shown), and the connecting portion 30*a* so that the X-ray shielding material mounting plates 3*a* and 3*b* do not interfere with them.

When the driving side link 5*b* is rotated by the rotational driving force of the motor 12, the X-ray shielding material mounting plates 3*a* and 3*b* are moved according to the rotation. As a result, the slit width is changed. FIGS. 4(*a*) and 5(*a*) show a state where the slit width is a minimum value 0, that is, the X-ray shielding materials 2*a* and 2*b* are in contact with each other to be completely shielded. When the driving side link 5*b* is rotated from this state by the rotational driving force of the motor rotary shaft 12*a* of the motor, the X-ray shielding material mounting plates 3*a* and 3*b* (and the X-ray shielding materials 2*a* and 2*b*) also move together in a direction in which the slit width increases, and the state of FIGS. 4(*a*) and 5(*a*) transitions to the state of FIGS. 4(*b*) and 5(*b*). When the driving side link 5*b* is further rotated, the slit width between the X-ray shielding material mounting plates 3*a* and 3*b* (and the X-ray shielding materials 2*a* and 2*b*) is increased up to the maximum value, and state transition to FIGS. 4(*c*) and 5(*c*) occurs.

According to the present embodiment, even if the driving side link 5*b* and the driven side link 5*a* are rotated and the X-ray shielding plate mounting plates 3*a* and 3*b* are moved according to the rotation so that the arbitrary slit width is obtained, the X-ray shielding material 2a and the X-ray shielding material mounting plate 3b, the X-ray shielding material 2b and the X-ray shielding material mounting plate 3a, and the X-ray shielding material mounting plates 3a and 3b and the driven side link 5a and the driving side link 5b do not interfere with each other since the connecting portion 13a, the collar 8a, and the connecting portion 30a are disposed within the cutout portions 14a and 14b and the connecting portion 13b, a collar (not shown), and the connecting portion 30b are disposed within the cutout portions 14c and 14d.

In addition, according to the present embodiment, since the X-ray shielding plate mounting plates 3a and 3b are made to cross each other and then are connected to each other using the driving side link 5b and the driven side link 5a, the change in width of the slit width with respect to the unit rotation angle of the rotary shaft of the motor is reduced as the slit width becomes narrow. Therefore, it is possible to further improve the adjustment accuracy of the slit width as the slit width becomes narrow.

In addition, it is possible to reduce the area of the X-ray shielding materials 2a and 2b by providing the X-ray shielding materials 2a and 2b in the X-ray shielding material mounting plates 3a and 3b. By reducing the volume of the X-ray shielding material that is generally expensive or is of great specific gravity, it is possible to realize a structure that is light and inexpensive compared with the related art.

In addition, by providing the cutout portions 14a, 14b, 14c, and 14d in the X-ray shielding material mounting plates 3a and 3b and disposing the driven side link 5a and the driving side link 5b within the cutout portions 14a, 14b, 14c, and 14d, it is possible to shorten the distance between the centers of the driven side link 5a and the driving side link 5b compared with a case where the driven side link 5a and the driving side link 5b are disposed outside the X-ray shielding material mounting plates 3a and 3b. As a result, size reduction can be achieved in a portion above the X-ray shielding material mounting plates 3a and 3b (on the X-ray tube 101 side).

Low friction materials 4a, 4b, 4c, and 4d are disposed on both surfaces of the X-ray shielding material mounting plates 3a and 3b, and are interposed from both the surfaces of the X-ray shielding material mounting plates 3a and 3b. Accordingly, even when the rotary disk 102 rotates at high speed to apply centrifugal force to the X-ray diaphragm mechanism 103, it is possible to prevent the inclination of the X-ray shielding material mounting plates 3a and 3b and the X-ray shielding material 2a, and 2b. As a result, the parallelism of the X-ray shielding materials 2a and 2b can always be maintained.

Second Embodiment

Figure 6:
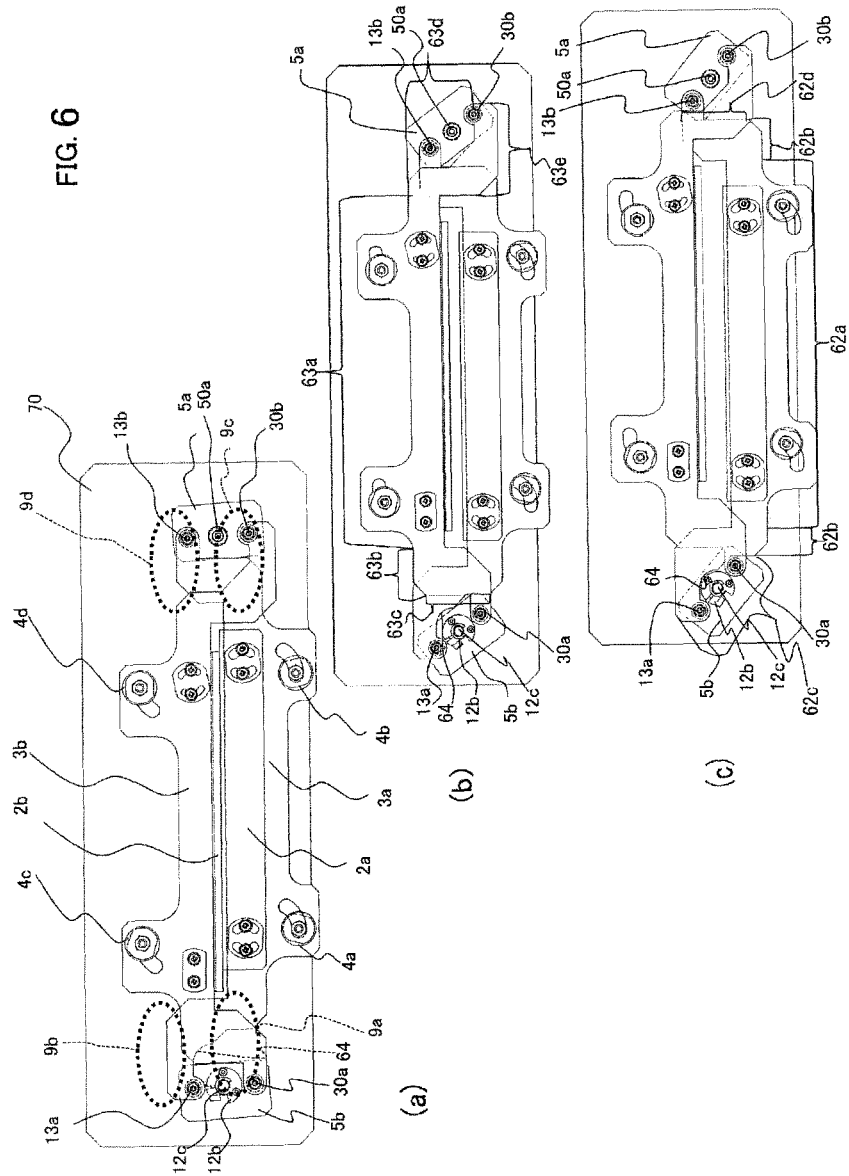
FIG. 6 is a state transition diagram showing, as a plan view, a state when the slit width of the X-ray diaphragm mechanism 103 according to a second embodiment changes, where (a) shows a state when the slit width is a minimum (complete shielding state), (b) shows a state between the maximum slit width and the minimum slit width, and (c) shows a state when the slit width is a maximum.
Figure 7:
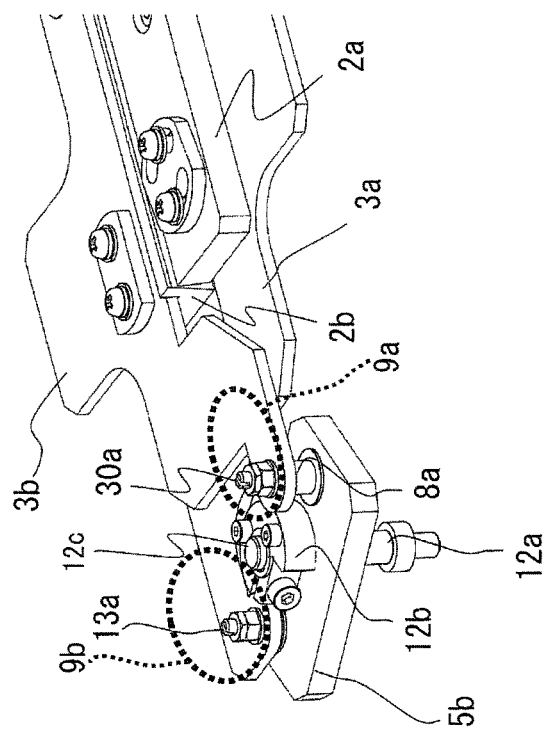
FIG. 7 is a partially enlarged view of the X-ray diaphragm mechanism 103 according to the second embodiment.

Next, a second embodiment will be described with reference to FIGS. 6 and 7. FIG. 6 is a state transition diagram showing, as a plan view, a state when the slit width of the X-ray diaphragm mechanism 103 according to the second embodiment changes, where (a) shows a state when the slit width is a minimum (complete shielding state), (b) shows a state between the maximum slit width and the minimum slit width, and (c) shows a state when the slit width is a maximum. FIG. 7 is a partially enlarged view of the X-ray diaphragm mechanism 103 according to the second embodiment.

Differences between the first and second embodiments are the shape of the X-ray shielding material mounting plates 3a and 3b and a method of setting the distance between the X-ray shielding materials 2a and 2b and the driven side link 5a and the driving side link 5b.

The X-ray shielding material mounting plates 3a and 3b according to the second embodiment include main body portions 62a and 63a for mounting the X-ray shielding materials 2a and 2b and flanges 9a, 9b, 9c, and 9d (in FIGS. 6 and 7, a partial region of each flange is drawn by the dotted line) from the main body portions 62a and 63a.

The two X-ray shielding material mounting plates 3a and 3b are disposed so as to face each other. The X-ray shielding material mounting plate 3a includes: the main body portion 62a extending in a longitudinal direction including a region for mounting the X-ray shielding material 2a; and the flange 9b provided at one end of the main body portion 62a along the longitudinal direction. The flange 9b includes a first arm portion 62b on the one end side that protrudes, from one end of the main body portion 62a along the longitudinal direction, in an opposite direction to a side where the main body portion 62a is located along the longitudinal direction. In addition, the flange 9b includes a second arm portion 62c, which protrudes in a direction away from the main body portion 62a so as to be oblique with respect to the longitudinal direction, on the end of the first arm portion 62b facing the X-ray shielding material mounting plate 3b in a state where the X-ray shielding material mounting plates 3a and 3b face each other. A partially arc-shaped cutout portion 64 is provided at the side end of the second arm portion 62c opposite the main body portion 62a. In addition, a protruding portion that protrudes in a direction perpendicular to the longitudinal direction and toward a side where the main body portion 62a is located is provided at the end of the second arm portion 62c opposite the main body portion 62a. That is, the flange 9b includes the first arm portion 62b, the second arm portion 62c, and the protruding portion. The protruding portion and the driving side link 5b are connected to each other by the connecting portion 13a formed of a connecting member, such as a screw.

The flange 9d is provided at the other end of the X-ray shielding material mounting plate 3a along the longitudinal direction. The flange 9d includes the first arm portion 62b on the other end side that protrudes, from the other end of the main body portion 62a along the longitudinal direction, in an opposite direction to a side where the main body portion 62a is located along the longitudinal direction. In addition, the flange 9d includes a third arm portion 62d, which protrudes in a direction perpendicular to the longitudinal direction and toward the facing X-ray shielding material mounting plate 3b, at the end of the first arm portion 62b facing the X-ray shielding material mounting plate 3b. A protruding portion that protrudes in a direction along the longitudinal direction and in an opposite direction to a side where the main body portion 62a is located is provided at the end of the third arm portion 62d opposite the main body portion 62a. That is, the flange 9d of the X-ray shielding material mounting plate 3a includes the first arm portion 62b on the other end side, the third arm portion 62d, and the protruding portion. The protruding portion and the driven side link 5a are connected to each other by the connecting portion 13b formed of a connecting member, such as a screw.

The X-ray shielding material mounting plate 3b includes the main body portion 63a extending in a longitudinal direction including a region for mounting the X-ray shielding material 2b and the flange 9a provided at one end of the main body portion 63a along the longitudinal direction. The flange 9a includes a first arm portion 63b that protrudes, from one end of the main body portion 63a along the longitudinal direction, in an opposite direction to a side where the main body portion 63a is located along the longitudinal direction. In addition, the flange 9a includes a second arm portion 63c protruding from the end of the first arm portion 63b facing the X-ray shielding material mounting plate 3a in a direction perpendicular to the longitudinal direction and toward the facing X-ray shielding material mounting plate 3a in a state where the X-ray shielding material mounting plates 3a and 3b face each other. A protruding portion that protrudes toward a side opposite the main body portion 63a along the longitudinal direction is provided at the end of the second arm portion 63c opposite the main body portion 63a. That is, the flange 9a includes the first arm 63b, the second arm portion 63c, and the protruding portion. The protruding portion and the driving side link 5b are connected to each other through the collar 8a (refer to FIG. 7), which is formed of a cylindrical member, and the connecting portion 30a formed of a connecting member, such as a screw. The connecting portion 30a passes through the cylindrical inside of the collar 8a, and connects the X-ray shielding material mounting plate 3b and the driving side link 5b to each other.

The flange 9c is provided at the other end of the X-ray shielding material mounting plate 3b along the longitudinal direction. The flange 9c includes a third arm portion 63d that protrudes toward a direction perpendicular to the longitudinal direction from the other end of the main body portion 63a along the longitudinal direction. In addition, the flange 9c includes a fourth arm portion 63e, which protrudes toward an opposite direction to a side where the main body portion 63a is located along the longitudinal direction, at the end of the third arm portion 63d opposite the main body portion 63a. A protruding portion that protrudes in a direction perpendicular to the longitudinal direction and toward a direction in which the main body portion 63a is located is provided at the end of the fourth arm portion 63e opposite the main body portion 63a. That is, the flange 9c includes the third arm portion 63d, the fourth arm portion 63e, and the protruding portion. The protruding portion and the driven side link 5a are connected to each other through a collar (not shown), which is formed of a cylindrical member having the same height as the collar 8a described above, and the connecting portion 30b formed of a connecting member, such as a screw. The connecting portion 30b passes through the cylindrical inside of the collar (not shown), and connects the X-ray shielding material mounting plate 3b and the driven side link 5a to each other.

In addition, the X-ray shielding material mounting plates 3a and 3b make the flanges 9a and 9b and the flanges 9c and 9d cross each other, and connect the flanges 9a and 9b to the driving side link 5b and connect the flanges 9c and 9d to the driven side link 5a. More specifically, parts of the first and second arm portions 62b and 62c on the one end side of the X-ray shielding material mounting plate 3a are made to cross the first and second arm portions 63b and 63c on the one end side of the X-ray shielding material mounting plate 3b with a difference in level therebetween. In addition, parts of the first and third arm portions 62b and 62d on the other end side of the X-ray shielding material mounting plate 3a are made to cross the third and fourth arm portions 63d and 63e of the X-ray shielding material mounting plate 3b with a difference in level therebetween.

The main characteristic points of the second embodiment are that the flanges 9a, 9b, 9c, and 9d are provided in the X-ray shielding material mounting plates 3a and 3b so as to cross each other so that the X-ray shielding material 2a and the X-ray shielding material mounting plate 3b, the X-ray shielding material 2b and the X-ray shielding material mounting plate 3a, and the X-ray shielding material mounting plates 3a and 3b and the driven side link 5a and the driving side link 5b do not interfere with each other in any slit width and that a sufficient distance between the X-ray shielding materials 2a and 2b and the driven side link 5a and the driving side link 5b is provided so that the movable region of the X-ray shielding materials 2a and 2b does not interfere with the rotational driving region of the driven side link 5a and the driving side link 5b.

The two X-ray shielding material mounting plates 3a and 3b are made to face each other, and the X-ray shielding material 2a is fixed to a surface of the X-ray shielding material mounting plate 3a facing the bed 105, and the X-ray shielding material 2b is fixed to a surface of the X-ray shielding material mounting plate 3b facing the X-ray tube 101. In addition, the open surfaces (opposite surfaces to surfaces fixed to the X-ray shielding material mounting plates 3a and 3b) of the X-ray shielding materials 2a and 2b are mounted so as to form the same plane.

The X-ray diaphragm mechanism 103 is fixed to a box-shaped collimator box 70 having an opening. An X-ray compensation filter (not shown) and the like are housed in the collimator box 70. The X-ray irradiation region is limited by matching the opening of the collimator box 70 with a gap (slit) between the X-ray shielding materials 2a and 2b and adjusting the slit width between the X-ray shielding materials 2a and 2b.

The link rotation center shaft 12c of the driving side link 5b is connected to the shaft 12a rotated by the motor 12. In addition, the boss 12b formed of a partially cut ring-shaped member is provided around the link rotation center shaft 12c, and the link rotation center shaft 12c is located in a hollow portion of the boss 12b. As shown in FIG. 6(a), in a state where X-rays are completely shielded, the X-ray shielding materials 2a and 2b are in contact with each other and there is no gap (slit width is a minimum value 0). When the shaft 12a is rotated (rotated forward) from this state, the rotational driving force is transmitted to the driving side link 5b and the driving side link 5b is driven to rotate. Then, the X-ray shielding material mounting plates 3a and 3b are moved in conjunction with the driving side link 5b, and the slit width is increased (refer to FIG. 6(b)). When the driving side link 5b is further driven to rotate and the slit width is excessively increased, the boss 12b comes in contact with the arc-shaped cutout portion 64 and the further rotational driving of the driving side link 5b is stopped, as shown in FIG. 6(c). That is, the cutout portion 64 functions as a so-called mechanical stopper. When the motor 12 rotates in the reverse direction, the driving side link 5b also rotates in the reverse direction. As a result, the slit width is decreased to transition to FIGS. 6(b) and 6(a).

According to the present embodiment, the flanges 9a, 9b, 9c, and 9d are provided in the X-ray shielding material mounting plates 3a and 3b, and the flanges 9a, 9b, 9c, and 9d are connected to the driven side link 5a and the driving side link 5b. Therefore, since the X-ray shielding material mounting plates 3a and 3b can be made small, it is possible to reduce weight. In addition, compared with a case where connection is performed in a cutout portion as in the first embodiment, it is possible to make the assembly of the X-ray shielding material mounting plates 3a and 3b and the driven side link 5a and the driving side link 5b easier.

By providing the X-ray shielding materials 2a and 2b in the X-ray shielding material mounting plates 3a and 3b, it is possible to reduce the area of the X-ray shielding material, compared with a case where the entire X-ray shielding material mounting plates 3a and 3b are formed by using the X-ray shielding material. By reducing the volume of the X-ray shielding material that is generally expensive or is of great specific gravity, it is possible to realize a structure that is light and inexpensive compared with the related art. In addition, both surfaces of the X-ray shielding material mounting plates 3a and 3b may be interposed from both sides by the low friction materials 4a, 4b, 4c, and 4d, the X-ray shielding material mounting plates 3a and 3b may be fixed to the collimator box 70 with the low friction materials 4a, 4b, 4c, and 4d interposed therebetween, and this state may be maintained. Accordingly, even when the rotary disk 102 rotates at high speed to apply the centrifugal force to the X-ray diaphragm mechanism 103, it is possible to prevent the inclination of the X-ray shielding material mounting plates 3a and 3b and the X-ray shielding material 2a, and 2b. As a result, the parallelism of the X-ray shielding materials can always be maintained.

Third Embodiment

Figure 8:
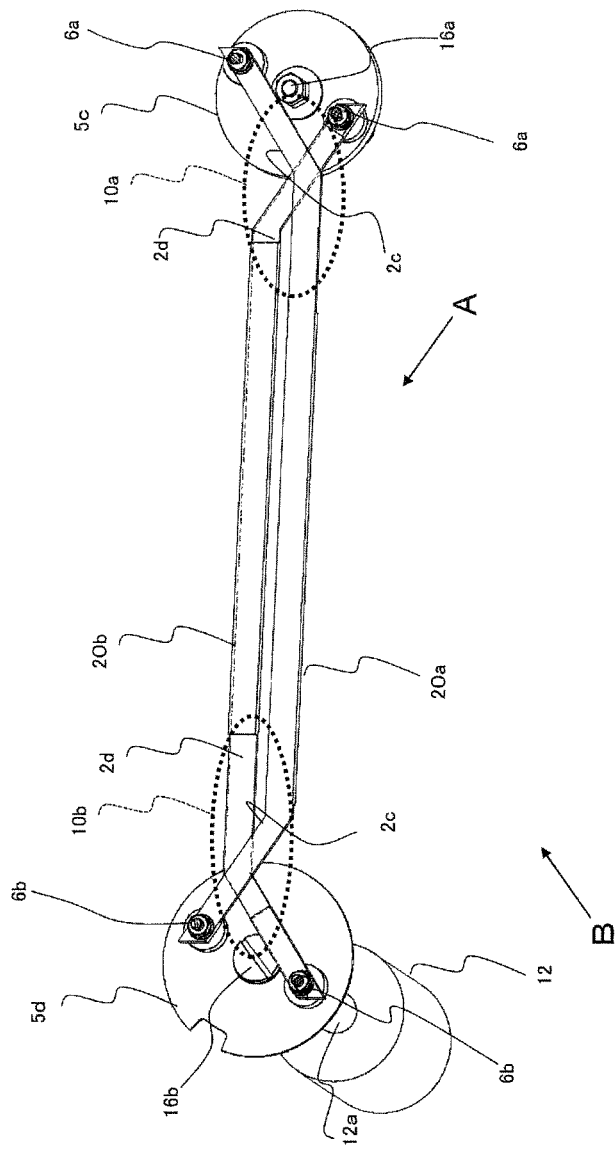
FIG. 8 is a perspective view of the X-ray diaphragm mechanism 103 according to a third embodiment.
Figure 9:
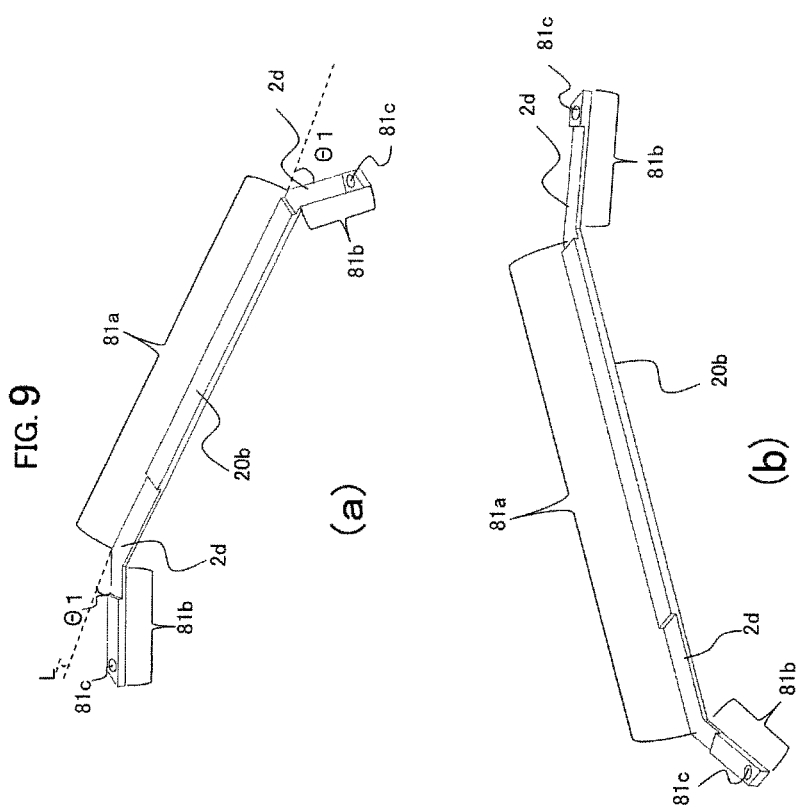
FIG. 9 is a single perspective view of an X-ray shielding material 2 shown in FIG. 8, where (a) shows an X-ray shielding material 20b when viewed from a direction of the arrow A in FIG. 8 and (b) shows the X-ray shielding material 20b when viewed from a direction of the arrow B in FIG. 8.

Next, a third embodiment will be described with reference to FIGS. 8 and 9. FIG. 8 is a perspective view of the X-ray diaphragm mechanism 103 according to the third embodiment. FIG. 9 is a single perspective view of an X-ray shielding material 20b shown in FIG. 8, where (a) shows the X-ray shielding material 20b when viewed from a direction of the arrow A in FIG. 8 and (b) shows the X-ray shielding material 20b when viewed from a direction of the arrow B in FIG. 8.

The main characteristics of the third embodiment are a point in which the X-ray shielding material mounting plate and the X-ray shielding material are integrally formed and a method of setting the distance between the driven side link and the driving side link.

As shown in FIG. 9, the X-ray shielding material 20b includes a main body portion 81a, which shields from X-rays and extends in a longitudinal direction, and a first arm portion 81b, which protrudes from both ends of the main body portion 81a in an oblique direction having an inclination of angle θ1 with respect to a reference line L along the longitudinal direction of the main body portion 81a. A hole 81c is provided at the end of each first arm portion 81b opposite the main body portion 81a. In addition, a groove 2d is provided from the main body portion 81a toward the first arm portion 81b. A bottom portion of the groove 2d is in a position lower than the top surface of the main body portion 81a.

An X-ray shielding material 20a includes a main body portion extending in a longitudinal direction and a first arm portion, which protrudes from both ends of the main body portion in an oblique direction having an inclination angle with respect to the reference line along the longitudinal direction of the main body portion. The X-ray shielding material 20a also includes a hole at the end of each first arm portion opposite the main body portion. In addition, a groove 2c is provided from the main body portion toward the first arm portion of the X-ray shielding material 20a. A bottom portion of the groove 2c is in a position lower than the top surface of the main body portion of the X-ray shielding material 20a. The shape of the X-ray shielding material 20a is approximately the same as the shape of the X-ray shielding material 20b, and the positions and lengths of the grooves 2c and 2d are slightly different.

As shown in FIG. 8, the two X-ray shielding materials 20a and 20b are made to cross each other at the grooves 2c and 2d. Therefore, the groove 2c is provided on the surface of the X-ray shielding material 20a facing the X-ray shielding material 20b. The groove 2d is provided on the surface of the X-ray shielding material 20b facing the X-ray shielding material 20a. In addition, one end of the X-ray shielding material 20b is connected to a driving side link 5d, which has a partially cut disc shape, through a shaft 6b passing through the hole 81c on the one end side. One end of the X-ray shielding material 20a is also connected to the driving side link 5d through the shaft 6b passing through a hole (not shown). A link rotation center 16b of the driving side link 5d is connected to the rotary shaft 12a of the motor 12. Two shafts 6b are provided at positions eccentric with respect to the link rotation center 16b.

The other end of the X-ray shielding material 20b is connected to a driven side link 5c through a shaft 6a passing through the hole 81c on the other end side. One end of the X-ray shielding material 20a is also connected to the approximately disc-shaped driven side link 5c through the shaft 6a passing through a hole (not shown). Two shafts 6a are provided at point-symmetrical positions with respect to a link rotation center 16a. In addition, the grooves 2c and 2d are provided in regions 10a and 10b where interference may occur in a region where the X-ray shielding materials 20a and 20b cross each other at the time of movement of the X-ray shielding materials 20a and 20b according to the rotational driving of the driving side link 5d.

When the driving side link 5d is driven to rotate by the motor 12, the driven side link 5c linked through the shaft 6b, the X-ray shielding materials 20a and 20b, and the shaft 6a is rotated, and the X-ray shielding materials 20a and 20b are moved. As a result, the slit width is changed. Since the above-described grooves 2c and 2d are provided in the regions 10a and 10b where interference may occur in a region where the X-ray shielding materials 20a and 20b cross each other, the X-ray shielding materials 20a and 20b are not in contact with each other at the time of movement of the X-ray shielding materials 20a and 20b. In addition, the open surfaces (surfaces facing the bed 105) of the X-ray shielding materials 20a and 20b can form the same plane by making the X-ray shielding materials 20a and 20b cross each other alternately in the grooves 2c and 2d.

By forming the shafts 6a and 6b, which connect the X-ray shielding materials 20a and 20b to the driven side link 5c and the driving side link 5d, as eccentric shafts, the parallelism of the two X-ray shielding materials 20a and 20b can be easily adjusted in a short time regardless of the amount of experience of the adjustment worker. In addition, the mechanism can be easily installed.

In addition, when the slit width becomes a maximum, the X-ray shielding materials 20a and 20b come in contact with the ends of the grooves 2c and 2d, respectively. Accordingly, movement in a direction in which the slit width of the X-ray shielding materials 20a and 20b is increased can be mechanically stopped.

According to the present embodiment, the end surfaces of the X-ray shielding materials 20a and 20b facing the bed 105 can be formed on the same plane by providing a groove in each of the X-ray shielding materials 20a and 20b and making the X-ray shielding materials 20a and 20b cross each other at the grooves. In addition, the collar used in the first and second embodiments is not necessary. In addition, by connecting the X-ray shielding materials 20a and 20b to the driven side link 5c and the driving side link 5d, the X-ray shielding material mounting plates 3a and 3b are not necessary unlike in the first and second embodiments. As a result, it is possible to reduce the number of components.

Fourth Embodiment

Figure 10:
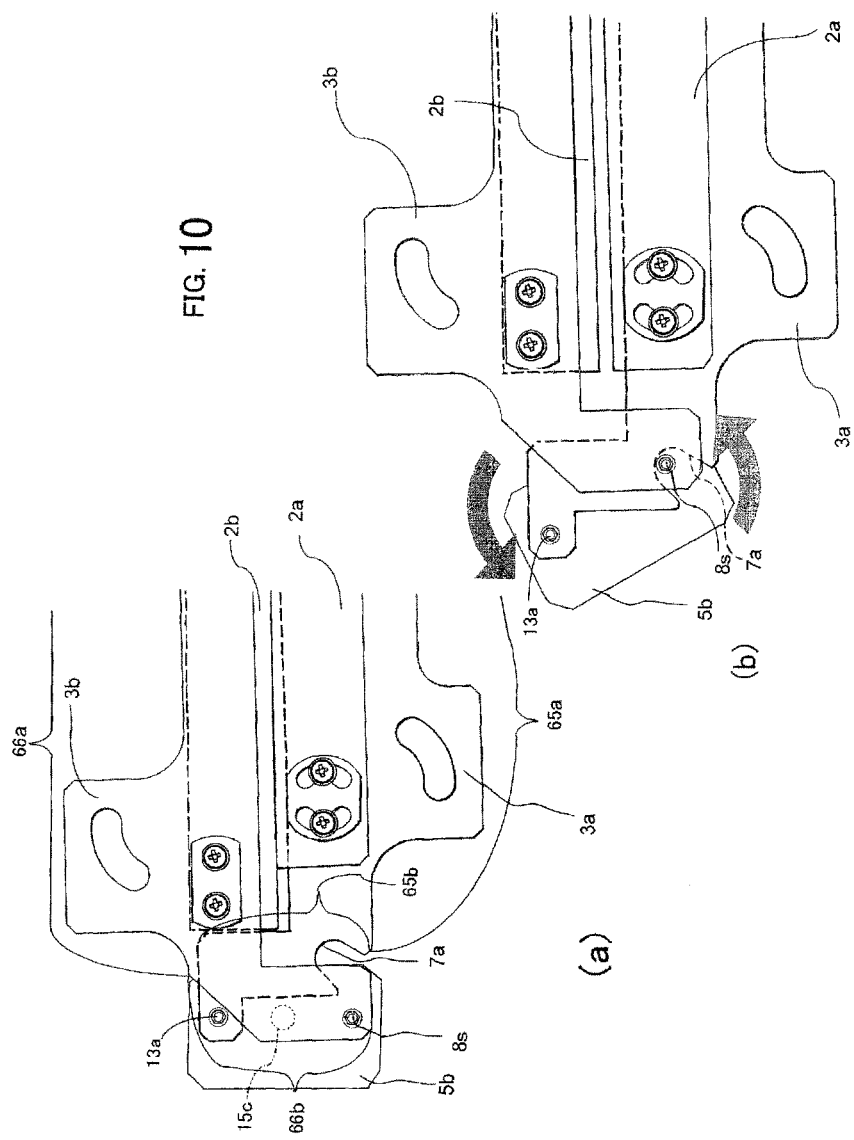
Figure 11:
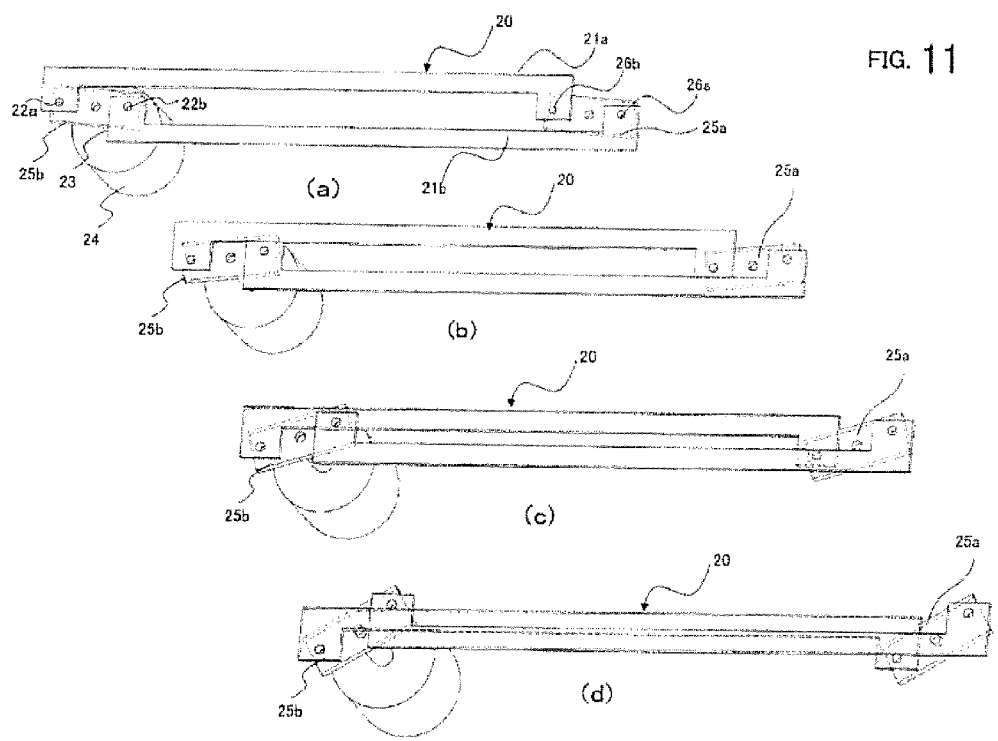
FIG. 11 is a state transition diagram for explaining the background art.

Next, a fourth embodiment will be described with reference to FIG. 10. FIG. 10 is a state transition diagram using a partially enlarged view of a plan view of the X-ray diaphragm mechanism 103 according to the fourth embodiment, where (a) shows a state when the slit width is a minimum (complete shielding state) and (b) shows a state where a stud 8s is inserted into a clearance groove 7a.

The X-ray shielding material mounting plate 3a includes: a main body portion 65a extending in a longitudinal direction including a region for mounting the X-ray shielding material 2a; and a first arm portion 65b protruding in a direction perpendicular to the longitudinal direction of the main body portion 65a as well as in a direction toward the facing X-ray shielding material mounting plate 3b. A protruding portion that protrudes toward a side opposite the main body portion 65a along the longitudinal direction is provided at the end of the first arm portion 5b opposite the main body portion 65a. The protruding portion and the driving side link 5b are connected to each other through the connecting portion 13a formed of a connecting member, such as a screw. The notch-shaped clearance groove 7a is provided at the end of the second arm portion 65b facing the main body portion 65a.

The X-ray shielding material mounting plate 3b includes a main body portion 66a extending in a longitudinal direction including a region for mounting the X-ray shielding material 2b and a first arm portion 66b protruding in a direction perpendicular to the longitudinal direction of the main body portion 66a and in a direction toward the facing X-ray shielding material mounting plate 3a. A collar (not shown) formed of a cylindrical member is disposed between the end of the first arm portion 66b opposite the main body portion 66a and the driving side link 5b. In addition, the end of the first arm portion 66b and the driving side link 5b are connected to each other by a connecting member passing through the inside of the collar, in the present embodiment, the stud 8s. Therefore, assuming that the driving side link 5b is a reference, a step equivalent to the height of a collar (not shown) is generated between the X-ray shielding material mounting plates 3a and 3b.

Although not shown in the drawing, the X-ray shielding material mounting plates 3a and 3b are also connected to the driven side link. In this case, the X-ray shielding material mounting plate 3b is connected to the driven side link 5a through a height adjustment member that gives the same step as the height of the above-described collar (not shown).

The driving side link 5b is connected to the rotary shaft of a motor at a link rotation center 15c. In addition, when the rotational driving force is transmitted to the link rotation center 15c through the rotary shaft of the motor, the driving side link 5b is driven to rotate and accordingly the X-ray shielding material mounting plates 3a and 3b are moved.

The clearance groove 7a is provided in a region where the stud 8s and the X-ray shielding material mounting plate 3a may interfere with each other at the time of movement of the X-ray shielding material mounting plates 3a and 3b. In addition, when the driving side link 5b is rotated and the X-ray shielding material mounting plates 3a and 3b are moved to enter the region where the X-ray shielding material mounting plate 3a and the stud 8s may interfere with each other, a collar (not shown) and the stud 8s are inserted into the clearance groove 7a. As a result, it is possible to avoid the interference as shown in FIG. 10(b).

When the slit width becomes a maximum, the collar (not shown) and the stud 8s come in contact with the deepest end in the clearance groove 7a. Then, the X-ray shielding material mounting plate 3b cannot move any more. As a result, it is possible to suppress a situation where the slit width becomes larger than the predetermined maximum width.

In addition, as in the first embodiment, the two X-ray shielding material mounting plates 3a and 3b are made to face each other, the X-ray shielding material 2a is fixed to a surface of the X-ray shielding material mounting plate 3a facing the X-ray shielding material mounting plate 3b (surface facing the bed 105), and the X-ray shielding material 2b is fixed to a surface of the X-ray shielding material mounting plate 3b facing the X-ray shielding material mounting plate 3a (surface facing the X-ray tube 101). In addition, the open surfaces of the X-ray shielding materials 2a and 2b are mounted so as to form the same plane.

According to the present embodiment, in the X-ray diaphragm mechanism in which the X-ray shielding material mounting plates 3a and 3b are disposed so as to cross each other with a difference in level therebetween, interference between the X-ray shielding material mounting plates 3a and 3b and a collar (not shown) and the stud 8s is avoided by providing the clearance groove 7a in the X-ray shielding material mounting plates 3a and 3b in advance. As a result, it is possible to avoid interference regardless of the shape of the X-ray shielding material mounting plates 3a and 3b.

In addition, it is possible to reduce the area of the X-ray shielding materials 2a and 2b by providing the X-ray shielding materials 2a and 2b in the X-ray shielding material mounting plates 3a and 3b. By reducing the volume of the X-ray shielding material that is generally expensive or is of great specific gravity, it is possible to realize a structure that is light and inexpensive compared with the related art.

While the embodiments of the present invention have been illustrated, the present invention is not limited to these, and various embodiments can be considered without departing from the scope of the present invention.

REFERENCE SIGNS LIST

1: X-ray CT apparatus
2: X-ray shielding material
3: X-ray shielding material mounting plate
4: low friction material
5: link (driven side link 5a, driving side link 5b)
6: shaft
7: clearance groove
8: collar
9: flange
10: groove
12: motor
100: scan gantry unit
101: X-ray tube
102: rotary disk
103: collimator
104: opening
105: bed
106: X-ray detector
107: data acquisition system
108: gantry controller
109: bed controller
110: X-ray controller
120: console
121: input device
122: image processing device
123: storage device
124: system controller
125: display device

The invention claimed is:
1. An X-ray diaphragm mechanism, comprising:
two X-ray shielding members each including an X-ray shielding portion, which is formed of an X-ray shielding material, a first peripheral portion located on one end side of the X-ray shielding portion in a longitudinal direction, and a second peripheral portion located on the other end side of the X-ray shielding portion in the longitudinal direction;

a first link that connects the first peripheral portions of the X-ray shielding members so that the first peripheral portions cross each other in X-ray incidence direction in a state where the X-ray shielding portions of the X-ray shielding members face each other and a second link that connects the second peripheral portions of the X-ray shielding members so that the second peripheral portions cross each other in the X-ray incidence direction in a state where the X-ray shielding portions of the X-ray shielding members face each other;

a first connecting portion that connects the first peripheral portion of each X-ray shielding member and the first link to each other and a second connecting portion that connects the second peripheral portion of each X-ray shielding member and the second link to each other; and a driving device that drives the first link or the second link so as to rotate, wherein a slit width between the X-ray shielding portions of the two X-ray shielding members is changed by moving the two X-ray shielding members in conjunction with rotational driving of the first and second links, and the first and second connecting portions are provided at positions not interfering with a movable region of the X-ray shielding member.

2. The X-ray diaphragm mechanism according to claim 1, wherein each of the first and second connecting portions includes a height adjustment member, and the height adjustment member is disposed between the first peripheral portion of one of the two X-ray shielding members and the first link and between the second peripheral portion of the one X-ray shielding member and the second link, and supports the one X-ray shielding member at a different height from the other X-ray shielding member.

3. The X-ray diaphragm mechanism according to claim 1, wherein each of the two X-ray shielding members has an approximately plate-shaped X-ray shielding plate, which is formed of an X-ray shielding material, and an X-ray shielding material mounting plate including a region for fixing the X-ray shielding plate between the first and second peripheral portions.

4. The X-ray diaphragm mechanism according to claim 3, wherein the first and second peripheral portions are disposed so as to bypass each rotation center of the first and second links, a portion where the first peripheral portions cross each other and a portion where the second peripheral portions cross each other are disposed on a side farther from the X-ray shielding plate than each rotation center of the first and second links, and each rotation center of the first and second links and the first and second connecting portions are disposed outside a movable region of the X-ray shielding material mounting plate.

5. The X-ray diaphragm mechanism according to claim 3, wherein each of the X-ray shielding material mounting plates includes a flange protruding in an opposite direction to the X-ray shielding plate from each of the first and second peripheral portions, and the first connecting portion connects the flange protruding from the first peripheral portion and the first link to each other, and the second connecting portion connects the flange protruding from the second peripheral portion and the second link to each other.

6. The X-ray diaphragm mechanism according to claim 3, wherein the first connecting portion includes a connector for connecting the first link and one of the X-ray shielding members to each other, and the other X-ray shielding member includes a clearance groove for avoiding interference with the facing connector in a region where interference with the connector may occur, and the connector is inserted into the clearance groove at the time of rotational driving of the first and second links.

7. The X-ray diaphragm mechanism according to claim 3, wherein the X-ray shielding plate is fixed to a surface of the one X-ray shielding material mounting plate facing the other X-ray shielding material mounting plate, the X-ray shielding plate is fixed to a surface of the other X-ray shielding material mounting plate facing the one X-ray shielding material mounting plate, and facing surfaces of the two X-ray shielding plates are disposed so as to form the same plane.

8. The X-ray diaphragm mechanism according to claim 1, wherein, in each of the two X-ray shielding members, the X-ray shielding portion and the first and second peripheral portions are integrally formed using an X-ray shielding material, the first peripheral portion of each X-ray shielding member includes a first arm portion that protrudes obliquely toward a direction away from the X-ray shielding portion with a shaft of the X-ray shielding portion, which is provided in each X-ray shielding member, along the longitudinal direction as a reference, the second peripheral portion of each X-ray shielding member includes a second arm portion that protrudes toward a direction away from the X-ray shielding portion with a shaft of the X-ray shielding portion, which is provided in each X-ray shielding member, along the longitudinal direction as a reference, the first arm portion provided in each X-ray shielding member includes a first groove for avoiding interference with the facing X-ray shielding member, the second arm portion provided in each X-ray shielding member includes a second groove for avoiding interference with the facing X-ray shielding member, the first connecting portion connects the first arm portion of each X-ray shielding member and the first link to each other in a state where the first arm portions of the two X-ray shielding members are made to cross each other at the first groove provided in each first arm portion, and the second connecting portion connects the second arm portion of each X-ray shielding member and the second link to each other in a state where the second arm portions of the two X-ray shielding members are made to cross each other at the second groove provided in each second arm portion.

9. The X-ray diaphragm mechanism according to claim 1, further comprising:

a stop mechanism portion that, when the slit width is increased to be greater than a maximum width, comes in contact with at least one of the two X-ray shielding members to mechanically stop movement of the X-ray shielding member in a direction in which the slit width is increased.

10. An X-ray CT apparatus, comprising:

the X-ray diaphragm mechanism according to claim 1;

an X-ray generation unit that generates X-rays;

an X-ray detector that detects the X-rays and outputs an image signal;

a rotation unit that rotates in a state where the X-ray generation unit, the X-ray diaphragm mechanism, and the X-ray detector are mounted; and an image reconstruction unit that generates a reconstructed image by performing image reconstruction processing on the basis of the image signal,
wherein the X-ray diaphragm mechanism limits an irradiation range of X-rays generated from the X-ray generation unit.

* * * * *